(12) United States Patent
Liu

(10) Patent No.: US 10,595,921 B2
(45) Date of Patent: Mar. 24, 2020

(54) SLIDING CROSS-FLUOROSCOPY AUXILIARY APPARATUS FOR INSERTING ORTHOPEDIC PEDICLE SCREW

(71) Applicant: Naixi Liu, Shandong (CN)

(72) Inventor: Naixi Liu, Shandong (CN)

( * ) Notice: Subject to any disclaimer, the term of this patent is extended or adjusted under 35 U.S.C. 154(b) by 0 days.

(21) Appl. No.: 16/090,113

(22) PCT Filed: Jun. 20, 2017

(86) PCT No.: PCT/CN2017/000390
§ 371 (c)(1),
(2) Date: Sep. 28, 2018

(87) PCT Pub. No.: WO2018/028142
PCT Pub. Date: Feb. 15, 2018

(65) Prior Publication Data
US 2019/0110827 A1    Apr. 18, 2019

(30) Foreign Application Priority Data
Aug. 8, 2016  (CN) .......................... 2016 1 0638753

(51) Int. Cl.
| A61F 2/46 | (2006.01) |
| A61B 17/88 | (2006.01) |
| A61B 17/92 | (2006.01) |
| A61B 6/00 | (2006.01) |
| A61B 34/20 | (2016.01) |
| A61B 17/70 | (2006.01) |

(Continued)

(52) U.S. Cl.
CPC ............ *A61B 17/8875* (2013.01); *A61B 6/00* (2013.01); *A61B 6/4014* (2013.01); *A61B 6/4225* (2013.01); *A61B 6/4441* (2013.01); *A61B 6/487* (2013.01); *A61B 17/7082* (2013.01); *A61B 17/92* (2013.01); *A61B 34/20* (2016.02); *A61B 6/06* (2013.01); *A61B 17/1757* (2013.01); *A61B 2017/90* (2013.01)

(58) Field of Classification Search
CPC combination set(s) only.
See application file for complete search history.

(56) References Cited

U.S. PATENT DOCUMENTS 6,104,780 A * 8/2000 Hanover ............. A61B 6/4014
378/92
2002/0007188 A1 1/2002 Arambula et al.
2002/0193686 A1 12/2002 Gilboa

FOREIGN PATENT DOCUMENTS

| CN | 2680212 | 2/2005 |
| CN | 104799933 | 7/2015 |

(Continued)

*Primary Examiner* — Sameh R Boles

(57) ABSTRACT

A sliding cross-fluoroscopy auxiliary apparatus includes: a holder (1) and a lifting pillar (2) on the holder (1), wherein a supporting arm (3) is provided on a top end of the lifting pillar (2), and a telescopic shaft (4) is arranged inside the supporting arm (3); a first end of the telescopic shaft (4) is connected to a first driver (5), and a second end of the telescopic shaft (4) is connected to an A arc (6); the first driver (5) drives the telescopic shaft (4) to extend out, draw back or rotate; a second driver (7) is arranged at a joint between the A arc (6) and the telescopic shaft (4), and a B arc (8) is placed between the second device (7) and the A arc (6); the second driver (7) drives the B arc (8) to rotate along the A arc (6).

7 Claims, 8 Drawing Sheets

(51) Int. Cl.
    *A61B 17/17*     (2006.01)
    *A61B 6/06*     (2006.01)
    *A61B 17/90*     (2006.01)

(56) References Cited

FOREIGN PATENT DOCUMENTS

| | | |
|---|---|---|
| CN | 204636394 | 9/2015 |
| CN | 205286513 | 6/2016 |

\* cited by examiner

SLIDING CROSS-FLUOROSCOPY AUXILIARY APPARATUS FOR INSERTING ORTHOPEDIC PEDICLE SCREW

CROSS REFERENCE OF RELATED APPLICATION

This is a U.S. National Stage under 35 U.S.C. 371 of the International Application PCT/CN2017/000390, filed Jun. 20, 2017, which claims priority under 35 U.S.C. 119(a-d) to CN 201610638753.4, filed Aug. 8, 2016.

BACKGROUND OF THE PRESENT INVENTION

Field of Invention

The present invention relates to a technical field of hospital orthopedic surgery auxiliary equipments, and more particularly to a sliding cross-fluoroscopy auxiliary apparatus for inserting an orthopedic pedicle screw.

Description of Related Arts

Conventionally, clinical fluoroscopy devices commonly used are "C" arm X-ray machines and "G" arm X-ray machines. The "C" arm X-ray machine can rotate, but it cannot see through both the front and side positions; the "G" arm can see through the front and side positions at the same time, but the position cannot be rotated. This has caused inconvenience to the surgical operation. Because of the inconvenience, manual placement of the pedicle screws is prone to errors. According to statistics, there is an observation that divided doctors into three groups of: experience less than 2 years, 2-5 years, and more than 5 years. In the absence of navigation technology, the pedicle screw failure rates of these three groups of doctors are very close, around 10%-12%. Therefore, it is easy to accidentally injure the dural sac and nerve root in the spinal canal, causing serious complications such as fistula and cerebrospinal fluid leakage, which brings pain to the patient and makes the doctor-patient relationship tense.

SUMMARY OF THE PRESENT INVENTION

An object of the present invention is to overcome defects of conventional technologies and provide a sliding cross-fluoroscopy auxiliary apparatus for inserting an orthopedic pedicle screw which improves positioning accuracy and decrease accidents.

Accordingly, in order to accomplish the above object, the present invention provides a sliding cross-fluoroscopy auxiliary apparatus for inserting an orthopedic pedicle screw, comprising: a holder and a lifting pillar on the holder, wherein a supporting arm is provided on a top end of the lifting pillar, and a telescopic shaft is arranged inside the supporting arm; a first end of the telescopic shaft is connected to a first driver, and a second end of the telescopic shaft is connected to an A arc; the first driver drives the telescopic shaft to extend out, draw back or rotate; a second driver is arranged at a joint between the A arc and the telescopic shaft, and a B arc is placed between the second device and the A arc; the second driver drives the B arc to rotate along the A arc; a third driver is arranged at a bottom end of the lifting pillar, which drives the lifting pillar to move up, move down or rotate;

wherein a first integrated tube and a first collimator are provided on a left end of the A arc, and a first image intensifier is provided on a right end of the A arc; axes of the first integrated tube, the first collimator and the first image intensifier coincide with each other; a second integrated tube and a second collimator are provided on an upper end of the B arc, and a second image intensifier is provided on a lower end of the B arc; axes of the second integrated tube, the second collimator and the second image intensifier coincide with each other;

wherein guiding devices are respectively provided at exterior sides of the first collimator and the second collimator, each of which comprises a guiding rod, a sliding cylinder, a connecting rod, and a sleeve cylinder; wherein a pedicle driller is arranged on the sleeve cylinder; bottom portions of the guiding rods are respectively connected to exterior sides of the first integrated tube of the A arc and the second integrated tube of the B arc, and axes of the guiding rods respectively coincide with the axes of the first collimator of the A arc and the second collimator of the B arc; the guiding rod passes through the sliding cylinder, which enables the sliding cylinder to move along the guiding rod or to lock the guiding rod; a first end of the connecting rod is connected to the sliding cylinder, and a second end of the connecting rod is connected to the sleeve cylinder; the guiding rod, the sliding cylinder, the sleeve cylinder and the pedicle driller share a same axis which coincides with axes of the first collimator, the second collimator, a ray source and a receiver the B arc guides an inserting direction of the orthopedic pedicle screw while the A arc prevents the orthopedic pedicle screw from excessive inserting; the A arc comprises the first integrated tube, both the A arc and the B arc comprise a fluoroscopy device, namely the integrated tubes, the collimators and the image intensifiers on both sides.

Preferably, the first driver comprises a first shaft, a first sleeve and a first base; a first shell is provided outside the first driver; a first bracing rod is connected between the first base and the lifting pillar; a first end of the first shaft is connected to the A arc and a second end of the first shaft is held by the first sleeve through a first bearing; a first rotating gear is provided on the first shaft; a first motor holder is provided on the first sleeve, and is at a right side of the first bearing and a left side of a first screw nut; a first rotating motor is placed on the first motor holder, whose output shaft is connected to a first gear shaft; the first gear shaft is engaged with the first rotating gear; a first screw rod driver is arranged at a bottom portion of the first sleeve, comprising the first screw nut, a first screw rod, and a first screw rod motor; wherein a first end of the first screw rod is sleeved on the first screw nut, and a second end of the first screw rod is connected to the first screw rod motor; when rotating, the first screw rod drives the first screw nut to move left or right, so as to drive the first sleeve to move left or right.

Preferably, the second driver comprises a second driving motor, a second reduction drive and a rack device; wherein the second reduction drive is connected to an output shaft of the second driving motor; the rack device comprises a driving gear connected to the output shaft of the second driving motor, and a rack placed on an inner arc surface of the B arc; the second driving motor drives the rack device to rotate the B arc along the A arc clockwise or anticlockwise.

Preferably, the third driver comprises a third shaft and a third sleeve on the lifting pillar; a third shell is provided outside the third driver; a first end of the third shaft is connected to a shell of the supporting arm, and a second end of the third shaft is held by the third sleeve through a third bearing; a third rotating gear is provided on the third shaft; a third motor holder is provided on the third sleeve, and is under the third bearing and above a third screw nut; a third rotating motor is placed on the third motor holder, whose output shaft is connected to a third gear shaft; the third gear shaft is engaged with the third rotating gear; a third screw rod driver is arranged at a bottom portion of the third sleeve, comprising the third screw nut, a third screw rod, and a third screw rod motor; wherein a first end of the third screw rod is sleeved on the third screw nut, and a second end of the third screw rod is connected to the third screw rod motor; when rotating, the third screw rod drives the third screw nut to move up or down, so as to drive the third sleeve to move up or down.

Preferably, universal wheels are arranged at four corners at a bottom portion of the holder; forward-backward wheels and left-right wheels are provided under the holder; a forward-backward transmission shaft is provided between the forward-backward wheels, and a left-right transmission shaft is provided between the left-right wheels; the forward-backward transmission shaft is under the left-right transmission shaft, wherein when the forward-backward wheels are raised and the left-right wheels are dropped, the forward-backward transmission shaft has no collision with the left-right transmission shaft; driving mechanisms are provided on both the forward-backward transmission shaft and the left-right transmission shaft; each of the driving mechanisms comprises a lifting mechanism and a rotating mechanism, wherein the lifting mechanism comprises a lifting cylinder and a screw rod mechanism, wherein the lifting cylinder is sleeved on a transmission shaft through an rolling bearing; the screw rod mechanism drives the lifting cylinder to move up or down; the rotating mechanism comprises a group of engaged gears and a rotating motor; the rotating motor is adhered to the transmission shaft through a motor holder, and the rotating motor drives the engaged gears to rotate, so as to rotate the forward-backward transmission shaft and the left-right transmission shaft.

Preferably, the sliding cross-fluoroscopy auxiliary apparatus further comprises: a controller, wherein telescopic shaft moving buttons, telescopic shaft rotating buttons, lifting pillar up-down buttons and lifting pillar rotating buttons are arranged on an upper portion of the controller; front-back-left-right buttons, forward-backward wheel up-down buttons, left-right wheel up-down buttons, B arc sliding buttons, a switch button, a first fluoroscopy button and a second fluoroscopy button are arranged on a lower portion of the controller.

The beneficial effect of the present invention is that the apparatus is used in conjunction with a display screen to facilitate accurate implantation of the pedicle screw and manipulation of the entire apparatus.

Figure 1:
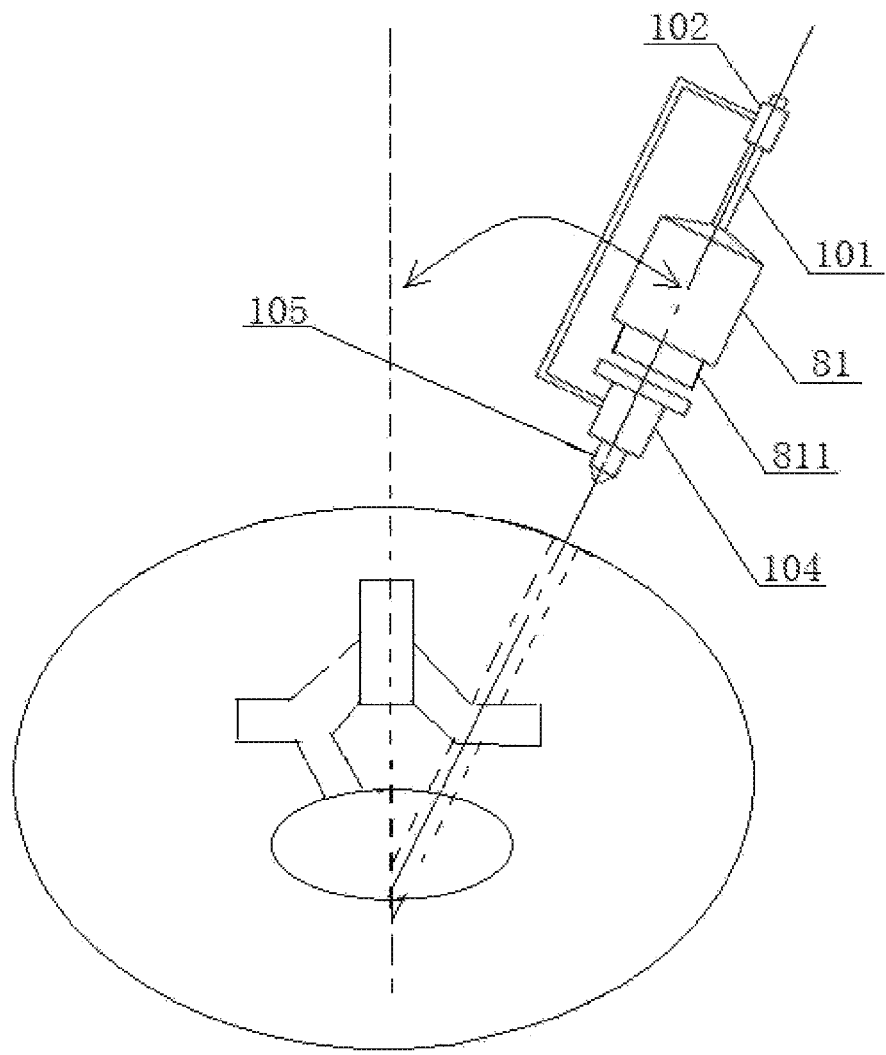
FIG. 1 is a sketch view of positions of a human spine cross-section and a device axis during a surgery.
Figure 2:
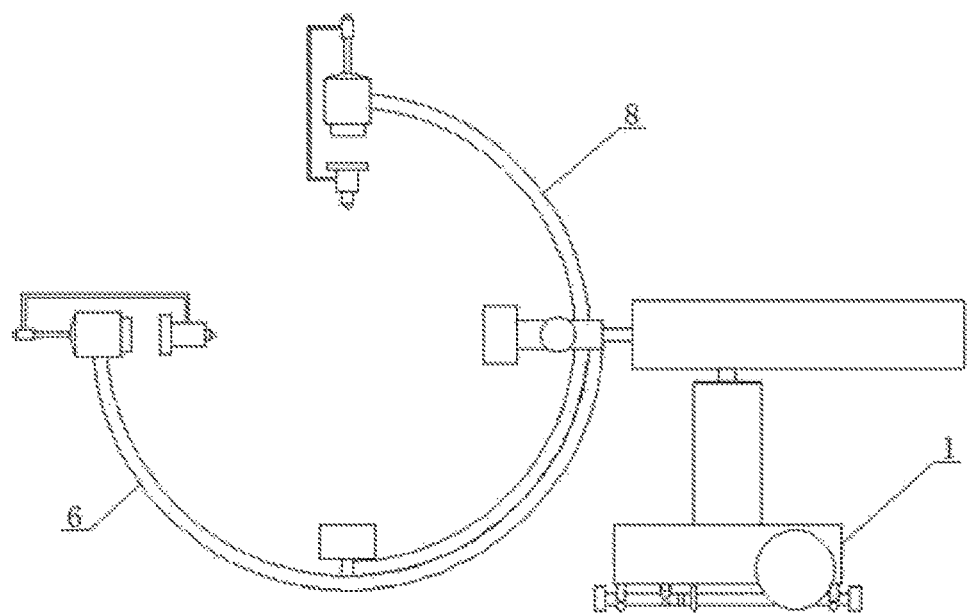
FIG. 2 is a sketch view of an overall structure of the present invention.
Figure 3:
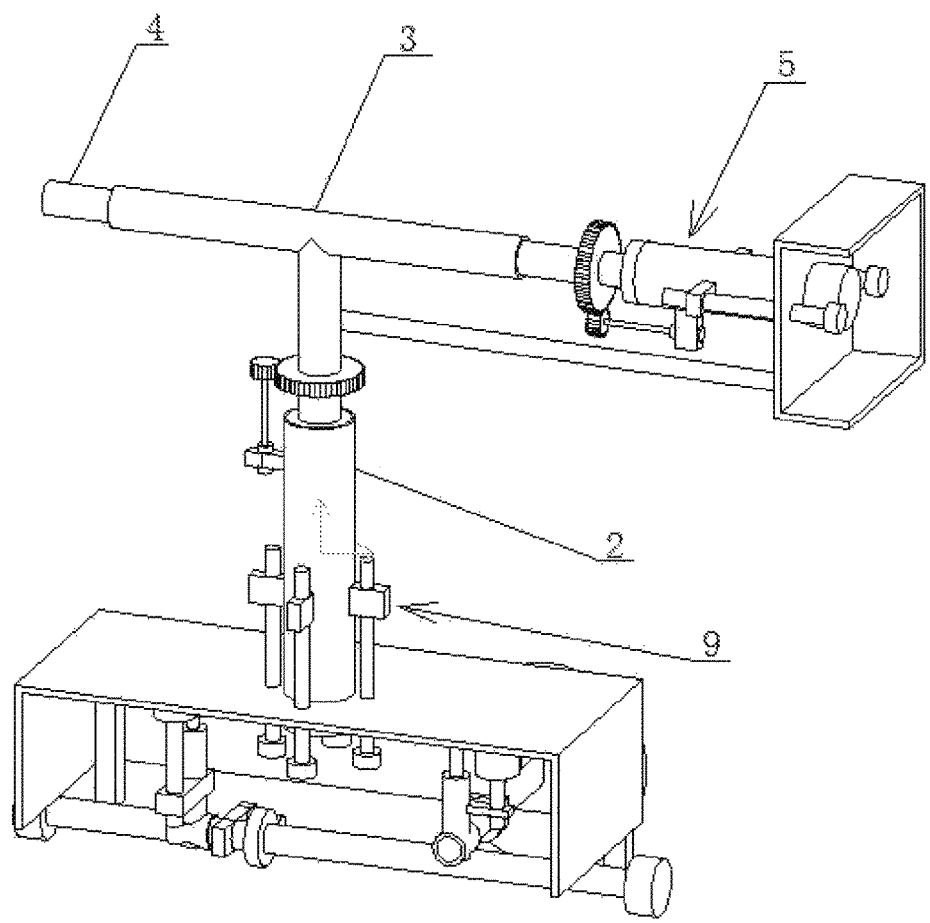
FIG. 3 is a structural view of a rear portion the present invention after removing a shell.
Figure 4:
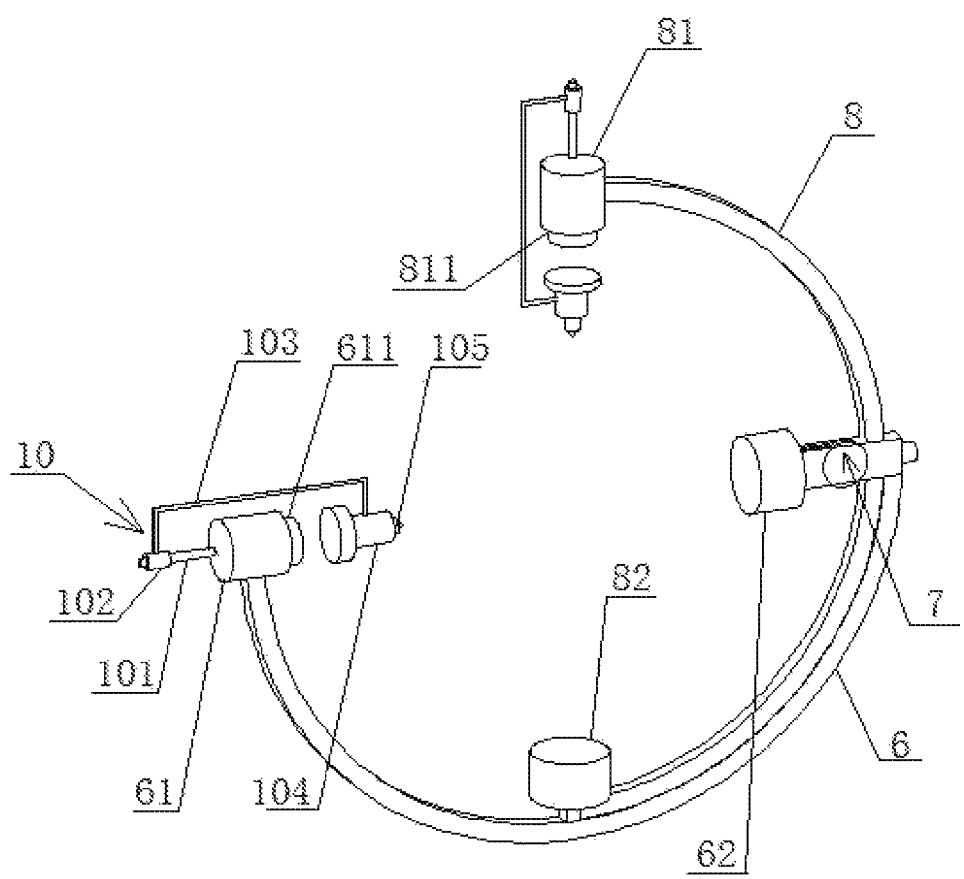
FIG. 4 is a structural view of an A arc and a B arc.
Figure 5:
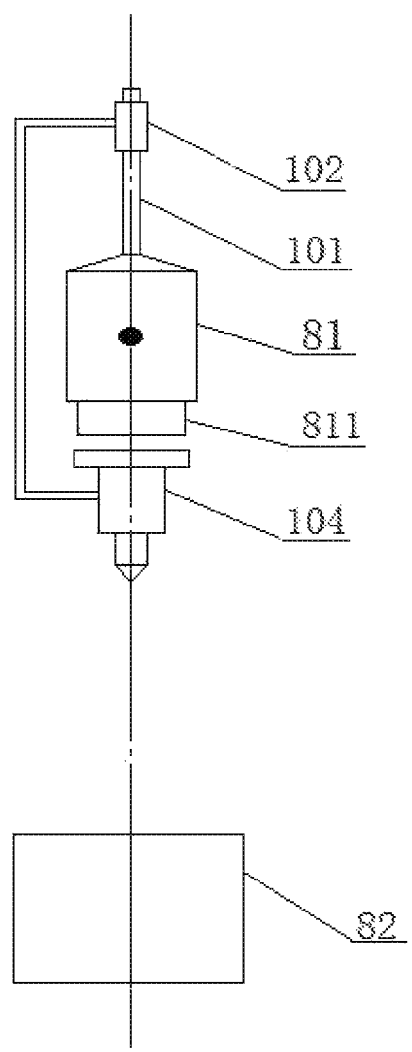
FIG. 5 is a sketch view of a coaxial state of a guiding rod, a sliding cylinder, a sleeve, a collimator, a pedicle driller, and an image intensifier.
Figure 6:
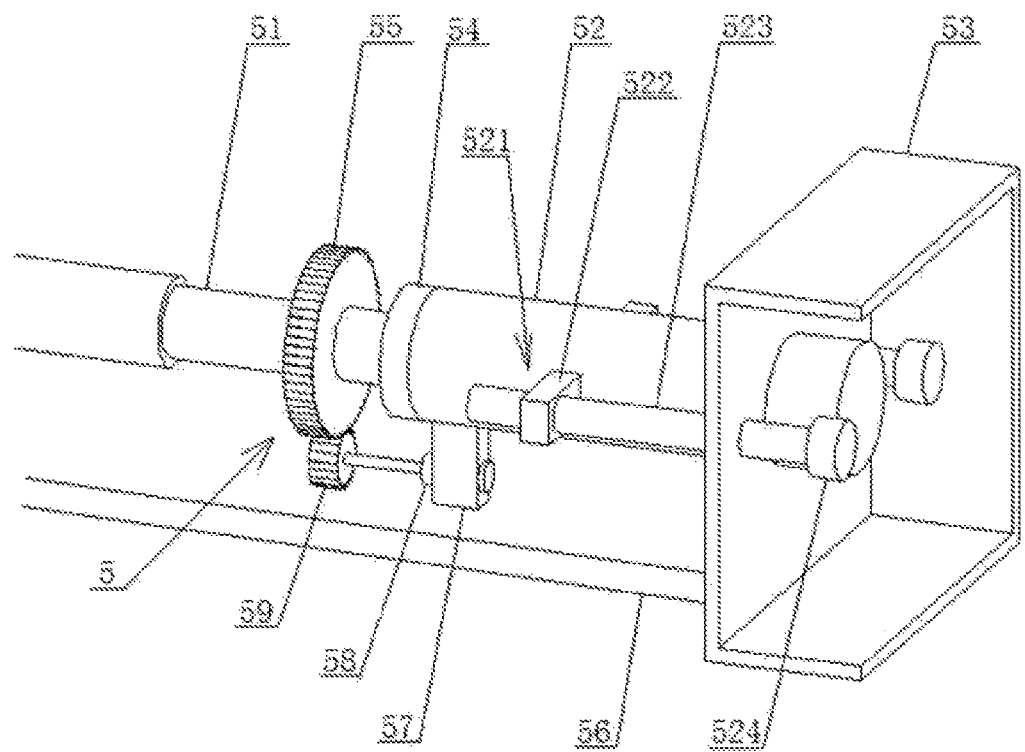
FIG. 6 is a structural view of a first driver.
Figure 7:
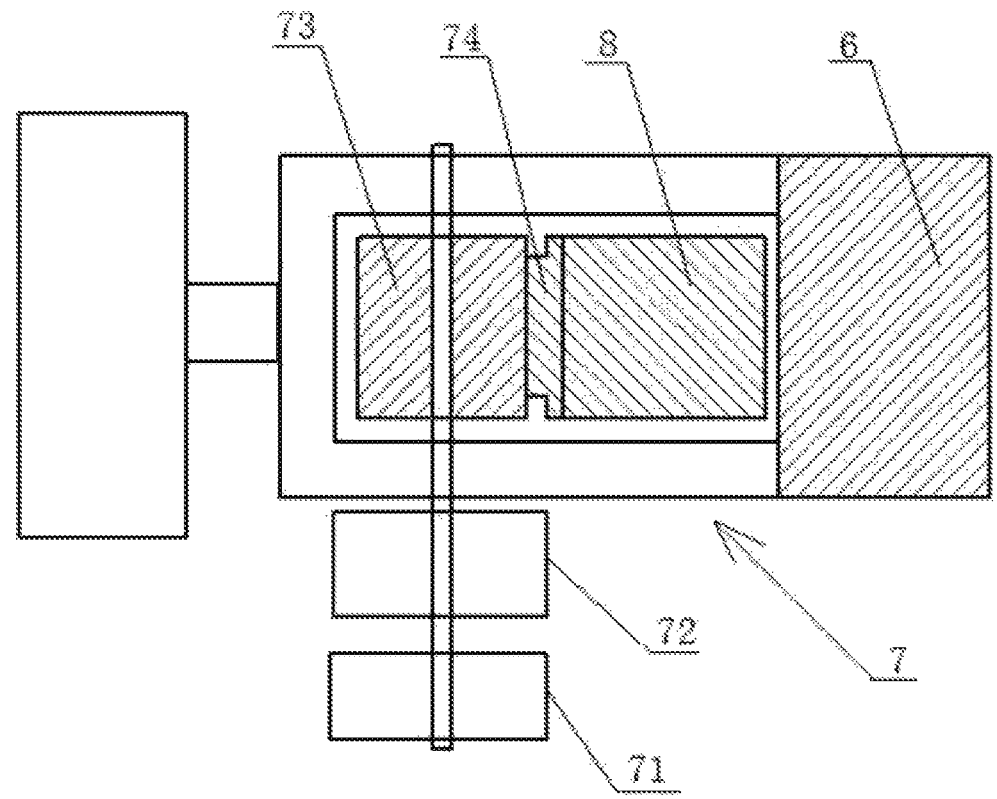
FIG. 7 is a cross-sectional view of a second driver.
Figure 8:
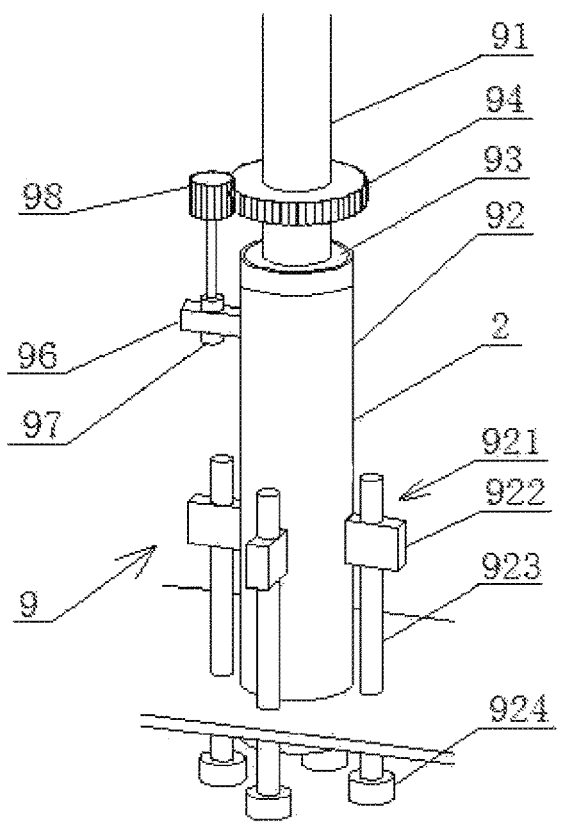
FIG. 8 is a structural view of a third driver.
Figure 9:
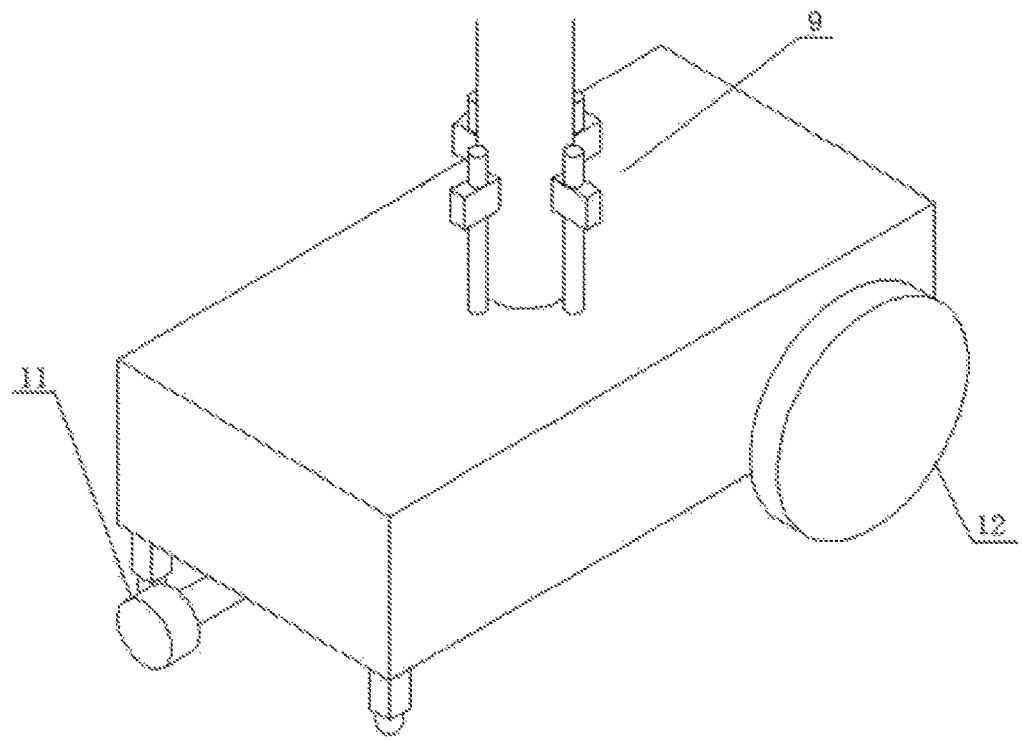
FIG. 9 is a schematic view of a holder.
Figure 10:
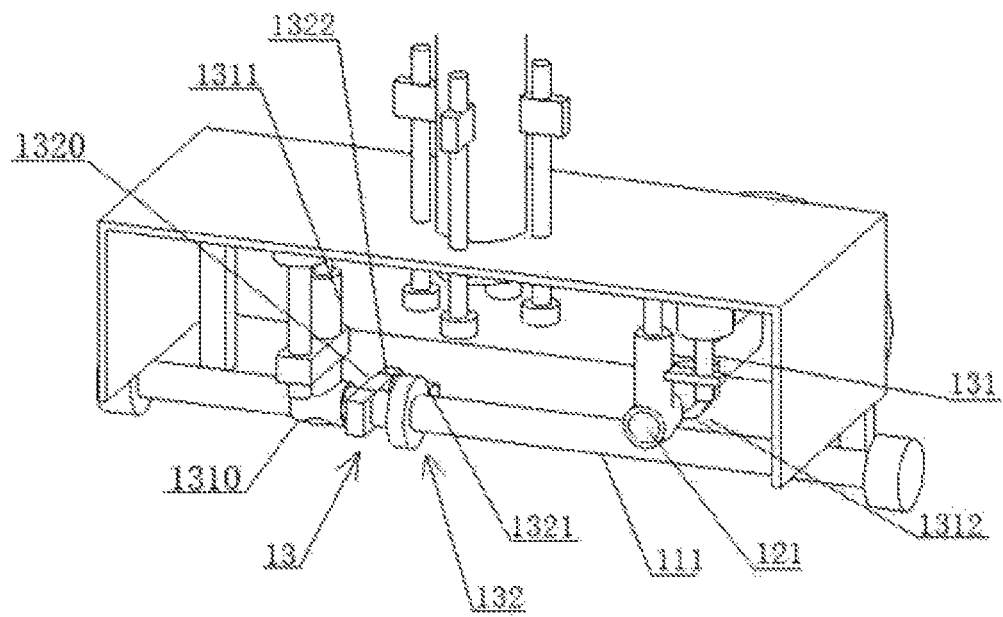
FIG. 10 is a sketch view of a base structure.
Figure 11:
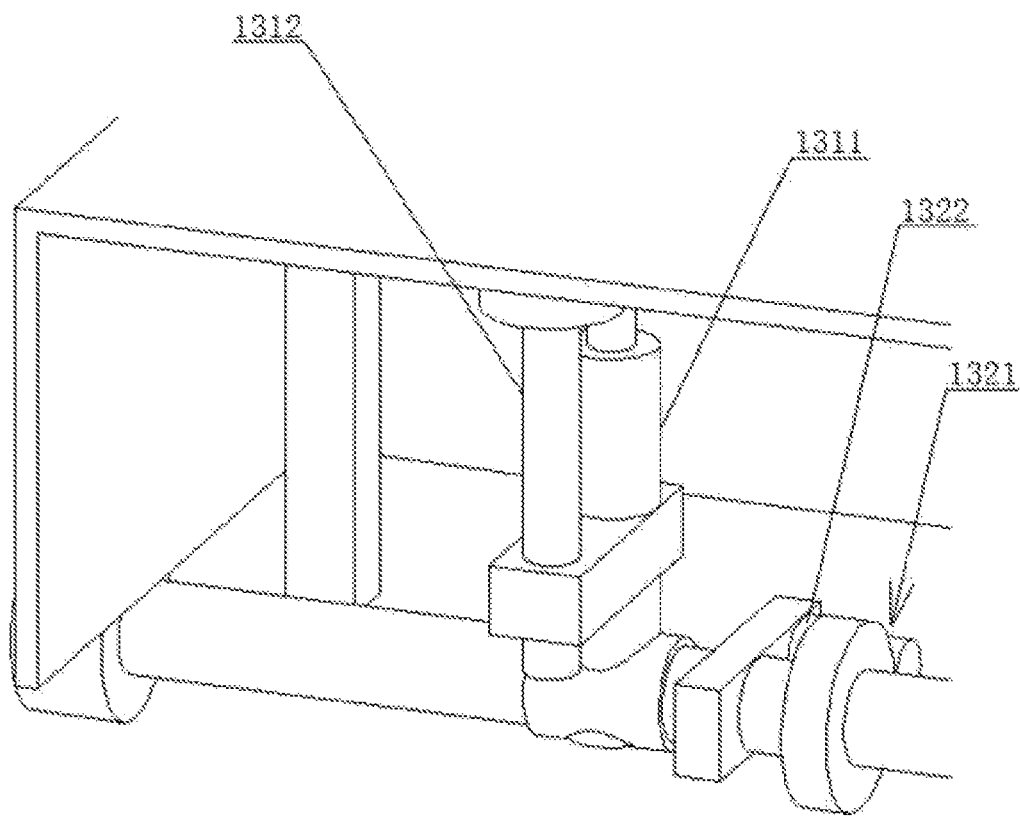
FIG. 11 is a partial enlarged view of the holder.
Figure 12:
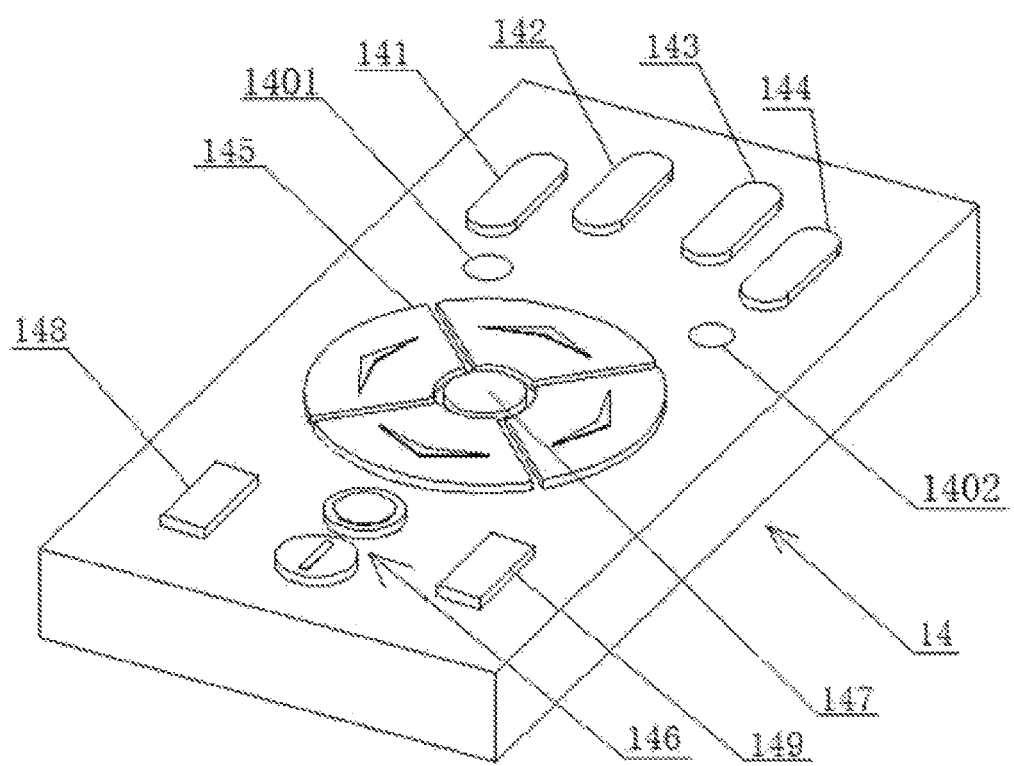
FIG. 12 is a structural view of a controller.

Element reference: 1—holder, 2—lifting pillar, 3—supporting arm, 4—telescopic shaft, 5—first driver, 50—first shell, 51—first shaft, 52—first sleeve, 521—first screw rod driver, 522—first screw nut, 523—first screw rod, 524—first screw rod motor, 53—first base, 54—first bearing, 55—first rotating gear, 56—first bracing rod, 57—first motor holder, 58—first rotating motor, 59—first gear shaft, 6—A arc, 611—first collimator, 61—first integrated tube, 62—first image intensifier, 7—second driver, 71—second driver motor, 72—second reduction drive, 73—driving gear, 74—rack, 8—B arc, 811—second collimator, 81—second integrated tube, 82—second image intensifier, 9—third driver, 90—third shell, 91—third shaft, 92—third sleeve, 921—third screw rod driver, 922—third screw nut, 923—third screw rod, 924—third screw rod motor, 93—third bearing, 94—third rotating gear, 96—third motor holder, 97—third rotating motor, 98—third gear shaft, 10—guiding device, 101—guiding rod, 102—sliding cylinder, 103—connecting rod, 104—sleeve cylinder, 105—pedicle driller, 11—forward-backward wheel, 12—left-right wheel, 111—forward-backward transmission shaft, 121—left-right transmission shaft, 13—driving mechanism, 131—lifting cylinder, 1310—rolling bearing, 1311—lifting rod, 1312—screw rod mechanism, 132—rotating mechanism, 1320—motor holder, 1321—engaged gear, 1322—rotating motor, 14—controller, 141—telescopic shaft moving button, 142—telescopic shaft rotating button, 143—lifting pillar up-down button, 144—lifting pillar rotating button, 145—front-back-left-right button, 146—switch button, 147—B arc sliding button, 148—forward-backward wheel up-down button, 149—left-right wheel up-down button, 1401—first fluoroscopy button, 1402—second fluoroscopy button.

DETAILED DESCRIPTION OF THE PREFERRED EMBODIMENT

Referring to the drawings, the present invention will be further illustrated as follows.

Embodiment 1

Referring to FIGS. 1-11, a sliding cross-fluoroscopy auxiliary apparatus for inserting an orthopedic pedicle screw is provided, comprising: a holder 1 and a lifting pillar 2 on the holder 1, wherein a supporting arm 3 is provided on a top end of the lifting pillar 2, and a telescopic shaft 4 is arranged inside the supporting arm 3; a first end of the telescopic shaft 4 is connected to a first driver 5, and a second end of the telescopic shaft 4 is connected to an A arc 6; the first driver 5 drives the telescopic shaft 4 to extend out, draw back or rotate; a second driver 7 is arranged at a joint between the A arc 6 and the telescopic shaft 4, and a B arc 8 is placed between the second device 7 and the A arc 6; the second driver 7 drives the B arc 8 to rotate along the A arc 6; a third driver 9 is arranged at a bottom end of the lifting pillar 2, which drives the lifting pillar 2 to move up, move down or rotate;

wherein a first integrated tube 61 and a first collimator 611 are provided on a left end of the A arc 6, and a first image intensifier 62 is provided on a right end of the A arc 6; axes of the first integrated tube 61, the first collimator 611 and the first image intensifier 62 coincide with each other; a second integrated tube 81 and a second collimator 811 are provided on an upper end of the B arc 8, and a second image intensifier 82 is provided on a lower end of the B arc 8; axes of the second integrated tube 81, the second collimator 811 and the second image intensifier 82 coincide with each other;

wherein guiding devices 10 are respectively provided at exterior sides of the first collimator 611 and the second collimator 811, each of which comprises a guiding rod 101, a sliding cylinder 102, a connecting rod 103, and a sleeve cylinder 104; wherein a pedicle driller 105 is arranged on the sleeve cylinder 104; bottom portions of the guiding rods 101 are respectively connected to exterior sides of the collimators of the A arc 6 and the B arc 8; the guiding rod 101 passes through the sliding cylinder 102, which enables the sliding cylinder 102 to move along the guiding rod 101 or lock the guiding rod 101 after moving to a certain position; a first end of the connecting rod 103 is connected to the sliding cylinder 102, and a second end of the connecting rod 103 is connected to the sleeve cylinder 104; the guiding rod 101, the sliding cylinder 102, the sleeve cylinder 104 and the pedicle driller 105 share a same axis which coincides with axes of the collimators, a ray source and a receiver; the pedicle driller 105 for clinical use is sleeved on the sleeve cylinder 104 for drilling on a pedicle following a ray; the B arc 8 guides an inserting direction of the orthopedic pedicle screw while the A arc 6 prevents the orthopedic pedicle screw from excessive inserting; both the A arc 6 and the B arc 8 comprise a fluoroscopy device, namely the integrated tubes, the collimators and the image intensifiers on both sides.

The first driver 5 comprises a first shaft 51, a first sleeve 52 and a first base 53; a first shell 50 is provided outside the first driver 5; a first bracing rod 56 is connected between the first base 53 and the lifting pillar 2; a first end of the first shaft 51 is connected to the telescopic shaft 4 and a second end of the first shaft 51 is held by the first sleeve 52 through a first bearing 54; a first rotating gear 55 is provided on the first shaft 51; a first motor holder 57 is provided on the first sleeve 52, and is at a right side of the first bearing 54; a first rotating motor 58 is placed on the first motor holder 57, whose output shaft is connected to a first gear shaft 59; the first gear shaft 59 is engaged with the first rotating gear 55; when rotating, the first rotating motor 58 drives the telescopic shaft 4 to rotate through the first gear shaft 59 and the first rotating gear 55, so as to tilt the A arc 6 and the B arc forwards or backwards; a first screw rod driver 521 is arranged at a bottom portion of the first sleeve 52, comprising a first screw nut 522, a first screw rod 523, and a first screw rod motor 524; wherein a first end of the first screw rod 523 is sleeved on the first screw nut 522, and a second end of the first screw rod 523 is connected to the first screw rod motor 524; when rotating, the first screw rod 523 drives the first screw nut 522 to move left or right, so as to drive the first sleeve 52 to move left or right, in such a manner that the first rotating gear 55 moves along an axial direction of the first gear shaft 5, which moves the telescopic shaft 4 forwards or backwards.

The second driver 7 comprises a second driving motor 71, a second reduction drive 72 and a rack device; wherein the second reduction drive 72 is connected to an output shaft of the second driving motor 71; the rack device comprises a driving gear 73 connected to the output shaft of the second driving motor 71, and a rack 74 placed on an inner arc surface of the B arc 8; the second driving motor 71 drives the rack device to rotate the B arc 8 along the A arc 6 clockwise or anticlockwise, in such a manner that the integrated tubes, the guiding devices and the pedicle of human spine are coaxial, as shown in FIG. 1.

The third driver 9 comprises a third shaft 91 and a third sleeve 92 on the lifting pillar 2; a third shell 90 is provided outside the third driver 9; a first end of the third shaft 91 is connected to a shell of the supporting arm 3, and a second end of the third shaft 91 is held by the third sleeve 92 through a third bearing 93; a third rotating gear 94 is provided on the third shaft 91; a third motor holder 96 is provided on the third sleeve 92, and is under the third bearing 93; a third rotating motor 97 is placed on the third motor holder 96, whose output shaft is connected to a third gear shaft 98; the third gear shaft 98 is engaged with the third rotating gear 94; when rotating, the third rotating motor 97 drives the third gear shaft 98 and the third rotating gear 94 to rotate the third rotating shaft 91, so as to rotate the telescopic shaft 4 in a horizontal plane, which swings the A arc 6 and the B arc 8 within the horizontal plane; a third screw rod driver 921 is arranged at a bottom portion of the third sleeve 92, comprising a third screw nut 922, a third screw rod 923, and a third screw rod motor 924; wherein a first end of the third screw rod 923 is sleeved on the third screw nut 922, and a second end of the third screw rod 923 is connected to the third screw rod motor 924; when rotating, the third screw rod 923 drives the third screw nut 922 to move up or down, so as to drive the third sleeve 92 to move up or down, in such a manner that the third rotating gear 94 moves along an axial direction of the third gear shaft 98, which moves the lifting pillar 2 up or down, thereby moving the A arc 6 and the B arc 8 to proper positions for surgery.

Universal wheels are arranged at four corners at a bottom portion of the holder 1; forward-backward wheels 11 and left-right wheels 12 are provided under the holder 1; a forward-backward transmission shaft 111 is provided between the forward-backward wheels 11, and a left-right transmission shaft 121 is provided between the left-right wheels 12; the forward-backward transmission shaft 111 is under the left-right transmission shaft 121, wherein when the forward-backward wheels 11 are raised and the left-right wheels are dropped 12, the forward-backward transmission shaft 111 has no collision with the left-right transmission shaft 121; driving mechanisms 13 are provided on both the forward-backward transmission shaft 111 and the left-right transmission shaft 121; each of the driving mechanisms 13 comprises a lifting mechanism 131 and a rotating mechanism 132, wherein the lifting mechanism 131 comprises a lifting cylinder 1311 and a screw rod mechanism 1312, wherein the lifting cylinder 1311 is sleeved on a transmission shaft through an rolling bearing 1310; the screw rod mechanism 1312 drives the lifting cylinder 1311 to move up or down, so as to move the forward-backward wheels 11 and the left-right wheels 12 up or down; the rotating mechanism 132 comprises a group of engaged gears 1321 and a rotating motor 1322; the rotating motor 1322 is adhered to the transmission shaft through a motor holder 1320, and the rotating motor 1322 drives the engaged gears 1321 to rotate, so as to rotate the forward-backward transmission shaft 111 and the left-right transmission shaft 121, thereby rotating the forward-backward wheels 11 and the left-right wheels 12.

The sliding cross-fluoroscopy auxiliary apparatus further comprises: a controller 14, wherein telescopic shaft moving buttons 141, telescopic shaft rotating buttons 142, lifting pillar up-down buttons 143 and lifting pillar rotating buttons 144 are arranged on an upper portion of the controller 14; front-back-left-right buttons 145, forward-backward wheel up-down buttons 148, left-right wheel up-down buttons 149, B arc sliding buttons 147, a switch button 146, a first fluoroscopy button 1401 and a second fluoroscopy button 1402 are arranged on a lower portion of the controller 14. Operating the B arc sliding buttons 147 enables the B arc 8 to slide along the A arc 6; operating the first fluoroscopy button 1401 and the second fluoroscopy button 1402 enables a motor on the left of the A arc 5 and a motor on the top of the B arc 8 to work, in such a manner that the image intensifiers receive X rays and output images to a screen; operating the telescopic shaft moving buttons 141 and the telescopic shaft rotating buttons 142 enables the telescopic shaft 4 to extend out, draw back and rotate; operating the lifting pillar up-down buttons 143 and the lifting pillar rotating buttons 144 enables the lifting pillar 2 to move up, move down or rotate; operating the front-back-left-right buttons 145 enables the whole apparatus to move forwards, backwards, left or right; operating the forward-backward wheel up-down buttons 148 and the left-right wheel up-down buttons 149 enables the forward-backward wheel 11 to rise from a ground and the left-right wheels 12 to rotate, or the left-right wheels 12 to rise from the ground and the forward-backward wheel 11 to rotate.

The apparatus is used in conjunction with a display screen to facilitate accurate implantation of the pedicle screw and remote manipulation of the entire apparatus.

What is claimed is:

1. A sliding cross-fluoroscopy auxiliary apparatus for inserting an orthopedic pedicle screw, comprising: a holder and a lifting pillar on the holder, wherein a supporting arm is provided on a top end of the lifting pillar, and a telescopic shaft is arranged inside the supporting arm; a first end of the telescopic shaft is connected to a first driver, and a second end of the telescopic shaft is connected to an A arc; the first driver drives the telescopic shaft to extend out, draw back or rotate; a second driver is arranged at a joint between the A arc and the telescopic shaft, and a B arc is placed between the second device and the A arc; the second driver drives the B arc to rotate along the A arc; a third driver is arranged at a bottom end of the lifting pillar, which drives the lifting pillar to move up, move down or rotate;

wherein a first integrated tube and a first collimator are provided on a left end of the A arc, and a first image intensifier is provided on a right end of the A arc; axes of the first integrated tube, the first collimator and the first image intensifier coincide with each other; a second integrated tube and a second collimator are provided on an upper end of the B arc, and a second image intensifier is provided on a lower end of the B arc; axes of the second integrated tube, the second collimator and the second image intensifier coincide with each other;

wherein guiding devices are respectively provided at exterior sides of the first collimator and the second collimator, each of which comprises a guiding rod, a sliding cylinder, a connecting rod, and a sleeve cylinder; wherein a pedicle driller is arranged on the sleeve cylinder; bottom portions of the guiding rods are respectively connected to exterior sides of the first integrated tube of the A arc and the second integrated tube of the B arc, and axes of the guiding rods respectively coincide with the axes of the first collimator of the A arc and the second collimator of the B arc; the guiding rod passes through the sliding cylinder, which enables the sliding cylinder to move along the guiding rod or to lock the guiding rod; a first end of the connecting rod is connected to the sliding cylinder, and a second end of the connecting rod is connected to the sleeve cylinder; the guiding rod, the sliding cylinder, the sleeve cylinder and the pedicle driller share a same axis which coincides with axes of the first collimator, the second collimator, a ray source and a receiver; the B arc guides an inserting direction of the orthopedic pedicle screw while the A arc prevents the orthopedic pedicle screw from excessive inserting; the A arc comprises a first fluoroscopy formed by the first integrated tube, the first collimator and the first image intensifier on both sides, and the B arc comprises a second fluoroscopy formed by the second integrated tube, the second collimator and the second image intensifier on both sides.

2. The sliding cross-fluoroscopy auxiliary apparatus, as recited in claim 1, wherein the first driver comprises a first shaft, a first sleeve and a first base; a first shell is provided outside the first driver; a first bracing rod is connected between the first base and the lifting pillar; a first end of the first shaft is connected to the A arc and a second end of the first shaft is held by the first sleeve through a first bearing; a first rotating gear is provided on the first shaft; a first motor holder is provided on the first sleeve, and is at a right side of the first bearing and a left side of a first screw nut; a first rotating motor is placed on the first motor holder, whose output shaft is connected to a first gear shaft; the first gear shaft is engaged with the first rotating gear; a first screw rod driver is arranged at a bottom portion of the first sleeve, comprising the first screw nut, a first screw rod, and a first screw rod motor; wherein a first end of the first screw rod is sleeved on the first screw nut, and a second end of the first screw rod is connected to the first screw rod motor; when rotating, the first screw rod drives the first screw nut to move left or right, so as to drive the first sleeve to move left or right.

3. The sliding cross-fluoroscopy auxiliary apparatus, as recited in claim 1, wherein the second driver comprises a second driving motor, a second reduction drive and a rack device; wherein the second reduction drive is connected to an output shaft of the second driving motor; the rack device comprises a driving gear connected to the output shaft of the second driving motor, and a rack placed on an inner arc surface of the B arc; the second driving motor drives the rack device to rotate the B arc along the A arc clockwise or anticlockwise.

4. The sliding cross-fluoroscopy auxiliary apparatus, as recited in claim 1, wherein the third driver comprises a third shaft and a third sleeve on the lifting pillar; a third shell is provided outside the third driver; a first end of the third shaft is connected to a shell of the supporting arm, and a second end of the third shaft is held by the third sleeve through a third bearing; a third rotating gear is provided on the third shaft; a third motor holder is provided on the third sleeve, and is under the third bearing and above a third screw nut; a third rotating motor is placed on the third motor holder, whose output shaft is connected to a third gear shaft; the third gear shaft is engaged with the third rotating gear; a third screw rod driver is arranged at a bottom portion of the third sleeve, comprising the third screw nut, a third screw rod, and a third screw rod motor; wherein a first end of the third screw rod is sleeved on the third screw nut, and a second end of the third screw rod is connected to the third screw rod motor; when rotating, the third screw rod drives the third screw nut to move up or down, so as to drive the third sleeve to move up or down.

5. The sliding cross-fluoroscopy auxiliary apparatus, as recited in claim 1, wherein universal wheels are arranged at four corners at a bottom portion of the holder; forward-backward wheels and left-right wheels are provided under the holder; a forward-backward transmission shaft is provided between the forward-backward wheels, and a left-right transmission shaft is provided between the left-right wheels; the forward-backward transmission shaft is under the left-right transmission shaft, wherein when the forward-backward wheels are raised and the left-right wheels are dropped, the forward-backward transmission shaft has no collision with the left-right transmission shaft; driving mechanisms are provided on both the forward-backward transmission shaft and the left-right transmission shaft, each of the driving mechanisms comprises a lifting mechanism and a rotating mechanism, wherein the lifting mechanism comprises a lifting cylinder and a screw rod mechanism, wherein the lifting cylinder is sleeved on a transmission shaft through an rolling bearing; the screw rod mechanism drives the lifting cylinder to move up or down; the rotating mechanism comprises a group of engaged gears and a rotating motor; the rotating motor is adhered to the transmission shaft through a motor holder, and the rotating motor drives the engaged gears to rotate, so as to rotate the forward-backward transmission shaft and the left-right transmission shaft.

6. The sliding cross-fluoroscopy auxiliary apparatus, as recited in claim 5, further comprising: a controller, wherein telescopic shaft moving buttons, telescopic shaft rotating buttons, lifting pillar up-down buttons and lifting pillar rotating buttons are arranged on an upper portion of the controller; front-back-left-right buttons, forward-backward wheel up-down buttons, left-right wheel up-down buttons, B arc sliding buttons, a switch button, a first fluoroscopy button and a second fluoroscopy button are arranged on a lower portion of the controller.

7. The sliding cross-fluoroscopy auxiliary apparatus, as recited in claim 1, further comprising: a controller, wherein telescopic shaft moving buttons, telescopic shaft rotating buttons, lifting pillar up-down buttons and lifting pillar rotating buttons are arranged on an upper portion of the controller; front-back-left-right buttons, forward-backward wheel up-down buttons, left-right wheel up-down buttons, B arc sliding buttons, a switch button, a first fluoroscopy button and a second fluoroscopy button are arranged on a lower portion of the controller.

\* \* \* \* \*